United States Patent [19]
Cheruvanky et al.

[11] Patent Number: 6,126,943
[45] Date of Patent: Oct. 3, 2000

[54] METHOD FOR TREATING HYPERCHOLESTEROLEMIA, HYPERLIPIDEMIA, AND ATHEROSCLEROSIS

[75] Inventors: Rukmini Cheruvanky, Folsom; Patricia McPeak; Reddy Sastry V. Cherukuri, both of El Dorado Hills, all of Calif.; Ike E. Lynch, Dillon, Mont.

[73] Assignee: The RiceX Company, El Dorado Hills, Calif.

[21] Appl. No.: 09/143,159

[22] Filed: Aug. 28, 1998

Related U.S. Application Data

[60] Provisional application No. 60/057,870, Sep. 2, 1997.

[51] Int. Cl.$^7$ .................................................. A61K 35/78
[52] U.S. Cl. ....................................................... 424/195.1
[58] Field of Search ........................... 424/195.1; 514/458

[56] References Cited

U.S. PATENT DOCUMENTS

| | | | |
|---|---|---|---|
| 4,358,462 | 11/1982 | Takeda | 426/13 |
| 4,952,568 | 8/1990 | Sawai et al. | 514/103 |
| 4,997,665 | 3/1991 | Grethlein | 426/543 |
| 5,118,503 | 6/1992 | Sawai et al. | 424/195.1 |
| 5,153,019 | 10/1992 | Hammond | 426/590 |
| 5,292,537 | 3/1994 | Hammond | 426/44 |
| 5,376,390 | 12/1994 | Hammond | 426/44 |
| 5,512,307 | 4/1996 | Hammond | 426/44 |
| 5,591,772 | 1/1997 | Lane et al. | 514/458 |
| 5,753,283 | 5/1998 | Hammond | 426/44 |
| 5,821,264 | 10/1998 | Lane et al. | 514/458 |

FOREIGN PATENT DOCUMENTS

| | | | |
|---|---|---|---|
| 0 457 539 B1 | 1/1994 | European Pat. Off. | A23L 1/308 |
| 62-201821 | 9/1987 | Japan | A61K 31/715 |
| 1-066203 | 3/1989 | Japan | C08B 37/00 |
| WO 93/09777 | 5/1993 | WIPO | A61K 31/355 |
| WO 98/17286 | 4/1998 | WIPO | A61K 31/715 |

OTHER PUBLICATIONS

Hegsted et al., FASEB J. 4(3): A368 (1990).

Mihara, S. (1970) "Nakataki Water Process for Separating Rice Bran Components," *Chemical Economy & Engineering Review* 2(9):36–39.

Zombade et al. (1983) "Nutritive Value of Raw, Parboiled, Stabilised and Deoiled Rice Bran for Growing Chicks" *J. Sci. Food Agric.* 34(8):783–788.

Yanagawa, et al., "A Method for Estimating Incidence Rates of Onchocerciasis from Skin–Snip Biopsies with Consideration of False Negatives," *Biometrics* 40:301–311 (Jun. 1984).

The Expert Panel, "Report of the National Cholesterol Education Program Expert Panel on Detection, Evaluation, and Treatment of High Blood Cholesterol in Adults," *Arch Intern Med* 148:36–69 (1988).

Marshall, W.E., et al. (editors), *Rice and Science Technology*, "IV. Stabilization and Processing," pp. 390–404 (1994).

Purushothama, S., et al., "Effect of Long Term Feeding of Rice Bran Oil upon Lipids and Lipoproteins in Rats," *Molecular and Cellular Biochemistry* 146(1):63–69 (1995).

Fan, Q., et al., "Nutritional Evaluation of Rice Bran Oil and a Blend with Corn Oil," *Die Nahrung* 39(5–6):490–496 (1995).

Cara, L., et al., "Effects of oat bran, rice bran, wheat fiber, and wheat germ on postprandial lipemia in healthy adults," *Am. J. Clin. Nutr.* 55:81–88 (1992).

*Primary Examiner*—Jean C. Witz
*Attorney, Agent, or Firm*—Townsend and Townsend and Crew LLP

[57] ABSTRACT

A method for reducing mammalian serum total cholesterol, LDL cholesterol, apolipoprotein B and triglyceride levels, by ingesting a stabilized rice bran derivative selected from the group consisting of an enzyme treated stabilized rice bran, an insolubilized fraction and mixtures thereof, thereby reducing serum total cholesterol, LDL cholesterol, apolipoprotein B and triglyceride levels in the mammal.

26 Claims, No Drawings

METHOD FOR TREATING HYPERCHOLESTEROLEMIA, HYPERLIPIDEMIA, AND ATHEROSCLEROSIS

RELATED APPLICATIONS

The present application claims the benefit of U.S. patent application Ser. No. 60/057,870, filed Sep. 2, 1997, the teachings of which are incorporated herein by reference.

1. Field of Invention

The present invention relates to methods for treating hypercholesterolemia, hyperlipidemia, and atherosclerosis in mammals by ingesting a stabilized rice bran derivative.

2. Background of the Invention

Hypercholesterolemia is a condition with elevated levels of circulating total cholesterol, LDL-cholesterol and VLDL-cholesterol as per the guidelines of the Expert Panel Report of the National Cholesterol Educational Program (NCEP) of Detection, Evaluation of Treatment of high cholesterol in adults (see, *Arch. Int. Med.* (1988) 148, 36–39). In particular, high levels of LDL and VLDL are positively associated with coronary arteriosclerosis while the high levels of high density lipoproteins (HDL) are negative risk factors. The role of LDL oxidation is gaining much attention in the literature. It is well documented that LDL becomes oxidatively stressed under pathological conditions and is no longer recognized by the LDL receptors. The oxidized LDL is taken up by macrophages within the subendothelial space, leading to the formation of fatty streaks which are the basis of most advanced lesions.

Hypercholesterolemia is implicated as a high risk factor of cardiovascular disease (CVD), including arteriosclerosis, atherosclerosis and xanthomatosis in humans. Hypercholesterolemia is influenced by diet, heredity, environment, life style, diseases and stress, leading to heart attacks and strokes at an early age.

Hyperlipidemia is a condition where the blood lipid parameters are elevated. The lipids fractions in the circulating blood are, total cholesterol (TC), low density lipoproteins (LDL), very low density lipoproteins (VLDL) and triglycerides (TG). As per the American Heart Association guidelines, the safe levels are represented below. Active treatment by diet modifications and drugs are necessary to reduce the risk of fatality when the levels go abnormal.

Total Cholesterol (TC) <240 mg/dL

LDL-C <160 mg/dL-Apo(B) Atherogenic factor

HDL-C >35 mg/dL Lp(a) Atherogenic factor

Triglycerides (TG) <150 mg/dL

Hyperlipidemia results from diet, heredity, lifestyle, environment, familial diseases, or stress. The condition may be inherited or may be secondary to another disorder, such as Systemic Lupus Erythematosus (SLE), Hypothyroidism, Nephrotic Syndrome, Cushing's Syndrome, Diabetes Mellitus, obesity, alcoholism, Corticosteroid Therapy or Estrogen Therapy.

Hyperlipidemia predisposes one to coronary heart disease, cancer and obesity. Hyperlipidemia is one of the high risk factors useful in the early diagnosis of these life threatening diseases. To some extent, hyperlipidemia can be corrected by diet modifications and treatment with drugs.

Atherosclerosis is a cardiovascular condition occurring as a result of narrowing down of the arterial walls. The narrowing is due to the formation of plaques (raised patches) or streaks in the inner lining of the arteries. These plaques consist of foam cells of low-density lipoproteins, oxidized-LDL, decaying muscle cells, fibrous tissue, clumps of blood platelets, cholesterol, and sometimes calcium. They tend to form in regions of turbulent blood flow and are found most often in people with high concentrations of cholesterol in the bloodstream. The number and thickness of plaques increase with age, causing loss of the smooth lining of the blood vessels and encouraging the formation of thrombi (blood clots). Sometimes fragments of thrombi break off and form emboli, which travel through the bloodstream and block smaller vessels.

The blood supply is restricted to the heart, eventually forming a blood clot leading to death. The major causes of atherosclerosis are hypercholesterolemia and hyperlipidemia is high circulating cholesterol and high lipids like LDL-cholesterol and triglycerides in the blood. These lipids are deposited in the arterial walls, obstructing the blood flow and forming atherosclerotic plaques leading to death.

Atherosclerosis is responsible for more deaths in the U.S. than any other single condition. Atherosclerotic heart disease involving the coronary arteries is the most common single cause of death, accounting for one third of all deaths. Atherosclerotic interference with blood supply to the brain (causing stroke) is the third most common cause of death after cancer. Atherosclerosis also causes a great deal of serious illness by reducing the blood flow in other major arteries, such as those to the kidneys, the legs and the intestines.

Medication is not a satisfactory treatment because much of the damage to the artery walls has already been done. Anticoagulant drugs have been used to try to minimize secondary clotting and embolus formation, but have little or no effect on the progress of the disease. Vasodilator drugs are used to provide symptom relief, but are of no curative value.

Surgical treatment is available for certain high-risk situations. Balloon angioplasty can open up narrowed vessels and promote an unproved blood supply. The blood supply to the heart muscle can also be restored through a vein graft bypass. Large atheromatous and calcified arterial obstructions can be removed by endarterectomy, and entire segments of diseased peripheral vessels can be replaced by woven plastic tube grafts.

With regard to reduction of hypercholesterolemia, in some instances this can be achieved by modification of the diet and/or use of drugs thereby minimizing the risk of fatality of the disease. Reduction of serum cholesterol in humans has been achieved by consumption of dietary plant fiber and other effective components of foods. However, there remains a need for a safe and effective treatment for the above conditions which are often interrelated with minimal risk or side effects. As a preventive cure, diet plays a crucial role in bringing down the lipid parameters. In addition to diet and exercise, there is a need for a supplemental therapy, possibly to prevent these conditions and insure better health, particularly in people who are genetically predisposed to such conditions. The present invention fulfills these and other needs.

SUMMARY OF THE INVENTION

It has now been surprisingly found that stabilized rice bran derivatives reduce serum total cholesterol, LDL cholesterol, apolipoprotein B and triglyceride levels in mammals. As such, the present invention provides a method for reducing mammalian serum total cholesterol, LDL cholesterol, apolipoprotein B and triglyceride levels, by ingesting a stabilized rice bran derivative such as, enzyme treated stabilized rice bran, an insolubilized fraction and mixtures thereof, thereby reducing serum total cholesterol, LDL cholesterol, apolipoprotein B and triglyceride levels. In one embodiment, the derivative is administered in an amount of about 10 grams to about 100 grams per day total in at least 2 doses.

In another aspect, the present invention provides a method for increasing the HDL/LDL cholesterol ratio in mammalian serum, by ingesting a stabilized rice bran derivative such as, an enzyme treated stabilized rice bran derivative, an insolubilized fraction and mixtures thereof, thereby increasing the HDL/LDL ratio.

In still yet another aspect, the present invention provides a process for making an enzyme treated stabilized rice bran derivative by mixing stabilized rice bran with an aqueous solution to form about a 15% to about a 35% aqueous rice bran slurry; adding an enzyme to the aqueous rice bran slurry to convert starch to dextrin, thereby forming an enzyme treated slurry, and then drying the enzyme treated slurry to form an enzyme treated stabilized rice bran derivative.

DESCRIPTION OF THE PREFERRED EMBODIMENT

I. Glossary

As used herein the term "apolipoprotein B" or "apoprotein B" or "Apo B" refers to the protein component of the LDL cholesterol transport proteins. Cholesterol synthesized de novo is transported from the liver and intestine to peripheral tissues in the form of lipoproteins. Most of the apolipoprotein B is secreted into the circulatory system as VLDL.

As used herein the term "arteriosclerosis" is a degeneration of the walls of the arteries due to the formation of foam cells and aortic streaks which narrow the arteries. This limits blood circulation and predisposes an individual to thrombosis.

As used herein the term "atherosclerosis" is a disease of the arteries in which fatty plaques develop on the inner walls, with eventual obstruction of blood flow.

As used herein the term "cardiovascular disease" is a disease of the blood vessels of the circulation system caused by abnormally high concentrations of lipids in the vessels.

As used herein the term "enzyme treated stabilized rice bran derivative" refers to an enzyme treated stabilized rice bran made by mixing a stabilized rice bran with an aqueous solution in a 15% to about a 35% aqueous slurry w/w; adding an enzyme to the aqueous rice bran slurry to convert starch to dextrin; and then directly drying the dextrin solution to form an enzyme treated stabilized rice bran derivative. The enzyme treated stabilized rice bran comprises about 20% to about 30% total dietary fiber.

As used herein the term "GRAS" means generally regarded as safe with respect to food additives.

As used herein the term "hypercholesterolemia" is a condition with elevated levels of circulating total cholesterol, LDL-cholesterol and VLDL-cholesterol as per the guidelines of the Expert Panel Report of the National Cholesterol Educational Program (NCEP) of Detection, Evaluation of Treatment of high cholesterol in adults (see, *Arch. Int. Med.* (1988) 148, 36–39).

As used herein the term "hyperlipidemia" or "hyperlipemia" is a condition where the blood lipid parameters are elevated in the blood. This condition manifests an abnormally high concentration of fats. The lipid fractions in the circulating blood are, total cholesterol, low density lipoproteins, very low density lipoproteins and triglycerides.

As used herein the term "lipoprotein" such as VLDL, LDL and HDL, refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

As used herein the term "stabilized rice bran derivative insolubilized fraction" refers to a fraction of stabilized rice bran during a partitioning process. Specifically, after the stabilized rice bran aqueous slurry is enzymatically treated as discussed fully below, it is then pumped into a centrifuge where the insoluble fraction precipitates out of the aqueous solution. The insoluble fraction is collected and then dried, and subsequently ground into a powder. This powder is the insoluble portion. In a preferred embodiment, the constituent parts and their percentages are listed in Tables I and IV.

As used herein the term "stabilized rice bran derivative solubilized fraction" refers to a fraction during a partitioning process. Specifically, after the stabilized rice bran aqueous slurry is enzymatically treated, it is then pumped into a centrifuge where the insoluble fraction precipitates out of the aqueous solution. The aqueous material is pumped to a dryer and then dried. This dried aqueous portion produces the soluble fraction. In a preferred embodiment, the constituent parts and their percentages are listed in Tables I and V.

As used herein the term "triglyceride" means a lipid or neutral fat consisting of glycerol combined with three fatty acid molecules.

As used herein the term "xanthomatosis" is a disease evidenced by a yellowish swelling or plaques in the skin resulting from deposits of fat. The presence of xanthomas are usually accompanied by raised blood cholesterol levels.

II. Detailed Description

In harvested rice, also known as rough rice, the kernel is completely enveloped by the rice hull. The milling process removes the hull, which yields brown rice. The outer brown layer is then removed by an abrasive milling process to generate white rice. The separated brown layer is designated rice bran.

Rice bran is the mesocarp, i.e., the portion between the hull and rice grain, obtained by milling or polishing brown rice. It constitutes about 10% of rough rice. It is generally used as an animal feed. It contains about 18–24% fat, about 25% dietary fiber, about 14% protein and about 45% total carbohydrates besides several potent micronutrients. It is rich in B-complex vitamins, vitamin E and its isomers, minerals like potassium, magnesium, and phosphorous besides several potent antioxidants.

Stabilized rice bran can be commercially purchased or prepared using various methods. Most stabilization methods of rice bran result in inactivation of the lipases which are present, inactivation of the peroxidases, and inactivation of the microorganisms, while still maintaining the high levels of antioxidants in the rice bran. For a general discussion of stabilization and processing see, *Rice Science and Technology,* edited by W. E. Marshall and James I Wadswoth, (1994) pages 390–404.

Under normal conditions when brown rice is milled to rice, the oil in the bran and the lipases also in the bran come into mutual contact, resulting in rapid degradation of the rice oil to free fatty acids and glycerol. The rice bran becomes unpalatable and is no longer suitable for foodstuffs. However, if the lipases are inactivated, the rice bran is thereby stabilized and the adverse effects on the bran are avoided.

There are many suitable means to stabilize or inactivate the lipase in rice bran, however most commercial systems utilize moisture-added or dry extrusion methods. These systems are selected because of their relatively low energy requirements, low capital costs and ease of operation. Stabilization by dry extrusion utilizes shear, friction, and pressure to generate the heat required to inactivate the lipase. The temperature of the bran must reach a temperature of a minimum of 130°–140° C. for up to 3 seconds to assure inactivation of the lipase.

Acceptable extrusion stabilization can be achieved under less harsh conditions by adding water or steam. The lipase is more heat sensitive at higher moisture and can therefore be inactivated at somewhat lower extrusion temperatures.

Residual peroxidase activity is generally used as the standard measure to make sure that lipase activity has been deactivated in stabilized rice bran. Peroxidase is generally considered to be more heat stable than lipase, and peroxidase activity assays are easier and more reliable than the assays for lipase. The process conditions required to inactivate peroxidase as well as lipase can also cause modification to or loss of antioxidants in the bran. This can lead to fewer fatty acids, but the bran can be subject to oxidative rancidity. In addition, because the rice bran is susceptible to mold, yeast and bacteria, the stabilization process must effectively reduce the microbiological load of the bran.

In addition to moisture added and extrusion techniques for stabilization, freezing and refrigeration of the rice bran result in economically viable processes to stabilize rice bran. Preferably, processes used to stabilize rice bran minimize the free fatty acid content, while maintaining high levels of antioxidants. Food grade stabilized rice bran is typically finely granulated, light tan in color and possesses a relatively bland flavor with a nutty, toasted overtones.

Stabilized rice bran is available commercially from Producers Rice Mill Inc. (Stuttgart, Ark.), Riceland Foods (Stuttgart, Ark.) Riviana Foods, Inc. (Houston, Tex.), Uncle Ben's Inc. (Houston, Tex.) and TheRiceX Company (El Dorado Hills, Calif.). Due to different stabilization processes, stabilized rice bran will differ in composition and stabilization characteristics when derived from different manufacturers.

In order to generate the rice bran derivatives for use in the present invention, the rice bran is first stabilized, and then it is further separated into at least two fractions. These include, but are not limited to, a stabilized rice bran soluble derivative and a stabilized rice bran insoluble derivative. Preferably, the separation into the rice bran derivatives includes a nonchemical process i.e., an enzymatic process. In this process, partitioning or fractionation preferably proceeds as outlined hereinafter.

The stabilized rice bran is made into about a 15% to about 35% slurry, preferably, a 20–25% slurry with potable water. An enzyme, which can include, but is not limited to, a dextranase, a maltase, a α-amylase, and various other carbohydrate cleaving enzymes, is added to the batch converting the starch to dextrins. The slurry is heated to about 150° F. to about 200° F. using for instance, a steam injection cooker, a heat exchanger or other heating method. The slurry is then pumped to a horizontal centrifuge wherein the insoluble fraction is separated. The insoluble fraction is collected and then dried on a belt dryer, and subsequently ground into a powder. This powder is the stabilized rice bran insoluble fraction. The aqueous material is pumped to a drum dryer and then dried. This dried aqueous portion produces the stabilized rice bran solubilized fraction.

The enzyme treated stabilized rice bran can be generated using the rice bran slurry as described above. As such, in another aspect, the present invention relates to the process for making an enzyme treated stabilized rice bran derivative, comprising: admixing stabilized rice bran with an aqueous solution to form about a 15% to about a 35% aqueous rice bran slurry, preferably a 20% to about a 30% aqueous rice bran slurry w/w; adding an enzyme to the aqueous rice bran slurry to convert starch to dextrin, thereby forming an enzyme treated slurry and then directly drying the enzyme treated slurry to form an enzyme treated stabilized rice bran derivative.

In a preferred embodiment of the foregoing process, after the enzyme is added to the slurry, the slurry is heated to about 100° F. to about 200° F. Preferably, the slurry is heated to about 150° F. to about 200° F. The slurry is then dried, wherein the drying is accomplished by a process such as belt drying, spray drying, drum drying and air drying. The drum drying process is preferred.

These stabilized rice bran derivatives are also available commercially from The RiceX Company of Calif. For the purpose of the invention, stabilized rice bran is available as RiceX™ Stabilized Rice Bran. The insoluble derivative is available as RiceX™ Fiber Complex and the soluble derivative is available as RiceX Ricelin™ from The RiceX Company, El Dorado Hills, Calif.

The stabilized rice bran derivatives can take a variety of forms. They can be a powder, a food, a food supplement, a medical food, a liquid, a beverage, an emulsion or mixture thereof. In addition, they can be incorporated into other edible materials. To incorporate the rice bran derivative into the diet of a mammal various options include, but are not limited to, simply sprinkling the derivative on another food substance (i.e., salad, bread, cereal, etc.) being a major ingredient in a multigrain ready to eat cereal, incorporating it into a baked product (breads, muffins, waffles, etc), or incorporating it into pasta, healthy dessert and snacks (athletic bar, healthy drink, etc.) and high fiber foods.

Stabilized rice bran contains about 18–23% fat, about 23–35% dietary fiber, about 12–16% protein, about 8–36% total carbohydrate and many potent microcomponents. Rice bran solubles contains about 15–40% fat, preferably 23–30% fat; about 0% to 25% dietary fiber, preferably about 0–20% dietary fiber; about 0% to 15% protein, preferably 6–9% protein and 25% to about 80% carbohydrates, preferably about 27–66% simple carbohydrate and is a water soluble fraction. Stabilized rice bran insoluble derivative contains about 5%–20% fat, preferably 11–16% fat; about 40–65% dietary fiber, preferably 40–60% dietary fiber, and about 10–30% protein, preferably 18–22% protein (see, Table I).

TABLE I

| COMPOSITION estimate | |
| --- | --- |
| RiceX Stabilized Rice Bran | |
| Fat | 18–23% |
| Protein | 12–16% |

TABLE I-continued

COMPOSITION estimate

| | |
|---|---|
| Total Dietary Fiber | 23–35% |
| Soluble Fiber | 2–6% |
| Carbohydrates | 8–36% |
| Ash | 7–10% |
| Moisture | 4–8 |
| RiceX Ricelin | |
| Fat | 23–30% |
| Protein | 6–9% |
| Total Dietary Fiber | 0–20% |
| Carbohydrates | 27–66% |
| Ash | 3–7% |
| Moisture | 2–7% |
| RiceX Fiber Complex | |
| Fat | 11–16% |
| Protein | 18–22% |
| Total Dietary Fiber | 40–60% |
| Soluble Fiber | 0–12% |
| Carbohydrates | 0–12% |
| Ash | 8–12% |
| Moisture | 1–6% |

With reference to Tables IV, V, VI and VII in Example 4, these derivatives have been shown to have at least seventy-five (75) potent anti-oxidants. The major antioxidant vitamin E and its isomers known as tocopherols (T) and tocotrienols ($T_3$) are collectively called tocols. A tocol rich substance is a mixture containing one or more compounds selected from tocopherols (T), tocotrienols ($T_3$), and tocotrienol-like ($T_3$-like) compounds.

Antioxidant in stabilized rice bran derivatives include, but are not limited to, γ-oryzanol, β-carotene, several known flavanoids, phytosterols, lipoic acid, and ferulic acid. Some of these compounds are present in high concentration, much more than in any of the known natural sources. It is believed that antioxidants particularly tocols, play a crucial role in significantly correcting certain metabolic disorders singularly or synergistically as discussed below.

The stabilized rice bran soluble derivative is a powdered emulsion of soluble stabilized rice bran and germ, and is easily digested and absorbed by the body. It can be taken by itself with a small amount of water to dissolve it in the mouth. It can also be mixed into liquids such as juice or hot drinks. Additionally, it is appropriate for use in baked goods and other foodstuffs as discussed above. There are a significant number of nutrients which have been discovered in rice bran solubles (stabilized rice bran solubilized derivatives).

The stabilized rice bran insoluble derivative binds bile acids thereby lowering serum cholesterol levels, and also decreases triglyceride levels thereby helping in the metabolism of cholesterol. It contains many highly potent antioxidants such as β-carotene, α, β, γ, and δ tocopherols and tocotrienols, phytate, oryzanols, glycosides and numerous phytosterols and polyphenols. The rice bran insoluble derivative can also be mixed into liquids such as juice or hot drinks. Additionally, it is appropriate for use in baked goods and other foodstuffs as discussed above.

The enzyme treated stabilized rice bran derivative can also be mixed into liquids such as juice or hot drinks. Additionally, it is appropriate for use in baked goods and other foodstuffs as discussed above.

The present invention is based on the discovery that persons suffering from hypercholesterolemia, hyperlipidemia, and atherosclerosis who ingest rice bran derivatives, such as the enzyme treated stabilized rice bran derivative, and stabilized rice bran insoluble derivative have significantly reduced serum total cholesterol, LDL cholesterol levels, apolipoprotein B and triglycerides. As such, the present invention relates to a method for reducing mammalian serum total cholesterol, LDL cholesterol, apolipoprotein B and triglyceride levels, the method comprises ingesting a stabilized rice bran derivative selected from the group consisting of an enzyme treated stabilized rice bran, an insolubilized fraction and mixtures thereof, thereby reducing serum total cholesterol, LDL cholesterol, apolipoprotein B and triglyceride levels in mammals. In a preferred embodiment, the mammal is a human individual.

It is presently preferred to administer the rice bran derivatives orally. In a preferred embodiment, the mammal ingesting the stabilized rice bran derivative is suffering from any number of diseases, including but not limited to, hyperlipidemia, cardiovascular disease, atherosclerosis, arteriosclerosis and xanthomatosis.

The stabilized rice bran derivative is ingested in an amount of about 10 grams to about 100 grams per day total, preferably in at least 2 doses. Preferably, the stabilized rice bran derivative is ingested in an amount of about 10 grams to about 40 grams per day total, and more preferably, in an amount of about 15 grams to about 30 grams per day total. The optimum dosage would be determined by the physician taking into account the age, weight and general health of the subject. The daily dosage can also be administered in one or several treatments over a period of time, such as by way of single or multiple doses per day or from sustained release compositions.

In another embodiment, the present invention relates to a method for increasing the HDL/LDL cholesterol ratio in mammalian serum comprising: ingesting a stabilized rice bran derivative selected from the group consisting of an enzyme treated stabilized rice bran derivative, an insolubilized fraction and mixtures thereof, thereby increasing said HDL/LDL cholesterol ratio in the mammal.

Elevated levels of LDL and VLDL are positively associated with coronary arteriosclerosis while the high levels of high density lipoproteins (HDL) are negative risk factors. Any dietary change which can decrease total cholesterol, LDL cholesterol levels will reduce risk of cardiovascular disease, atherosclerosis, arteriosclerosis and xanthomatosis. Thus, in this aspect, ingesting a stabilized rice derivative in an amount of about 10 grams to about 100 grams per day total, preferably in at least 2 doses will reduce the HDL/LDL ratio.

The stabilized rice bran derivative can be ingested alone or, more usually, in the form of a foodstuff comprising a therapeutically effective amount of the stabilized rice bran derivative in combination with an inert GRAS food component and an acceptable diluent or carrier therefor.

The stabilized rice bran derivative can also be used in association with other therapeutic agents including, for example, antibiotics or antiviral agents.

The potent antioxidants in stabilized rice bran derivatives, namely Vitamin E and its isomers, in combination with the other antioxidants present in it, play a major role in treating atherosclerosis by reducing the cholesterol levels, lipid levels, preventing platelet aggregation, preventing LDL-oxidation and restoring good blood supply to the heart.

The major antioxidants T and $T_3$ are thought to inhibit a key enzyme, HMG CoA reductase, in liver microsomes involved in the biosynthetic pathway of cholesterol. The mechanism of $T_3$, in inhibiting HMG CoA reductase involve post-transcriptional suppression of HMG CoA reductase in a manner mimicking the action of putative non-sterols feedback inhibitors.

Without being bound to a particular theory, it is believed that the bioactive components in rice bran derivatives, and their associated mechanisms, positively effect the management of atherosclerosis, cardiovascular disease and the associated conditions of hypercholesterolemia and hyperlipidemia. These bioactives seem to act synergistically, creating an enhanced effect not expected when one evaluates the individual compounds present in rice bran derivatives. The major bioactive components present in the rice bran derivatives are tocopherols, tocotrienols, γoryzanol, phytosterols, polyphenols, inositol, B vitamins, protein, fiber, and fat (see, Tables IV–VII). Some of the biological effects of these components and the mechanisms involved are set forth below.

1. Enzyme inhibitions: three enzymes, namely HMGCoA reductase, ACAT transferase and esterase are inhibited. HMGCoA reductase, a key enzyme involved in the cholesterol biosynthesis is inhibited by the tocotrienols, post transcriptionally, reducing the synthesis of cholesterol resulting in low circulating cholesterol.

Acyl coenzyme A transferase (ACAT), inhibition is brought about by γ-oryzanol leading to:
 a) the prevention of cellular cholesterol esterification thereby enriching high density lipoprotein cholesterol (HDL) with free cholesterol;
 b) elevation of HDL, a positive effect, and decreased synthesis of very low density lipoprotein cholesterol (VLDL); and
 c) increased clearance of cholesterol as bile acids and bile salts.

The net result is lower circulating cholesterol. Cholesterol esterases are inhibited by cycloartenol, a component of γ-oryzanol, resulting in a slower hydrolysis of cholesterol esters and decreased absorption. This results in lower circulating total cholesterol.

2. γ-Oryzanol inhibits platelet aggregation, and aortic streaks thus reducing atherosclerosis.

3. Rice bran derivatives contain a significant variety and concentration of antioxidants. Antioxidants such as tocopherols, tocotrienols, γ-oryzanol, polyphenols as ferulic acid, and lipoic acid are involved in the repair of free radical damage, preventing low density lipoprotein cholesterol (LDL) oxidation, resulting in the reduction of vascular damage that can lead to cardiovascular disease.

4. Cycloartenol, a component of γ-oryzanol, has a structure similar to cholesterol and competes with receptor sites of cholesterol. This causes a sequestration of cholesterol as bile salts and bile pigments, thus maintaining lower levels of circulating cholesterol.

5. Phytosterols and fiber facilitate cholesterol sequestration from the body through increased excretion of bile salts and bile acids, resulting in lower levels of circulating cholesterol. The effect of soluble fiber in cholesterol management is well documented in the literature.

6. The protein, fat (with high levels of polyunsaturated and monounsaturated fatty acids), and B vitamins also contribute to the hypocholesterolemic effect.

III. EXAMPLES

Example 1

This example illustrates a clinical evaluation of stabilized rice bran derivatives in a statistically significant population. Moreover the effect of RiceX Stabilized Rice Bran, RiceX Ricelin (stabilized rice bran soluble derivative) and RiceX Fiber Complex (stabilized rice bran insoluble derivative) on blood glucose and lipid concentration in human subjects. This clinical evaluation was carried out at the Advanced Medical Research center at Madison, Wis. and at the Armed Forces Institute of Pathology, Rawalpindi, Pakistan.

MATERIAL AND METHODS

A. Product Description

RiceX Rice Bran, RiceX Ricelin and RiceX Fiber Complex are products rich in fiber, non-starchy polysaccharides, complex carbohydrates, proteins, fats, B-complex vitamins, and potent antioxidants such, as β-carotene, vitamin E (Tocopherols and Tocotrienols), γ-oryzanol, phytosterols, and polyphenols.

B. Product Codes

Product A: RiceX Stabilized Rice Bran;

Product B: RiceX Ricelin;

Product C: RiceX Fiber Complex

C. Subjects

Subjects selected were individuals with clinically established cases of diabetes mellitus (Type I or Type II), male or female, between the age of 20–65 years, with ideal body weight (+20%), and no diagnosed complications. The subjects were under glycemic control with either oral hypoglycemic agents, or insulin therapy or both. All the subjects were on National Cholesterol Education Program (NCEP) step-1 diet.

D. Dosage and Duration

The subjects were initially screened and randomly assigned to the $Rice_x$ product regimen. Test product was provided to each subject in two equally divided doses of 10 grams each, one taken before breakfast and one taken before dinner in milk/fruit juice/water beverage. The total dosage of 20 grams per day was provided to each subject every day for eight weeks.

E. Study Protocol

The products were given at random either in sequence, or individually for eight weeks. When subjects were evaluated on more than one product a washout period of four weeks with a cellulose placebo to replace treatment was used before switching to the next product. An initial fasting blood sample was drawn before each product regimen, and a final fasting blood sample was drawn at the end of each product regimen. These blood samples were used for the measurement of glycemic and lipid parameters. Physical parameters such as body weight, body mass index, height, medications, and diet were measured and recorded for each subject. Blood glucose levels were monitored every morning before breakfast and every evening before dinner, by the subjects drawing capillary blood and using a glucometer. Any significant change, like sudden hypoglycemic episodes were managed by reducing the medications as well as the rice bran products on which the subjects were maintained, as recommended by the study physician.

F. Biochemical Analysis

The initial and final blood samples of all the subjects before and after the treatment of each product were collected and stored at −80° C. until analyzed. These samples were analyzed for glycosylated hemoglobin, glucose, insulin, total cholesterol, LDL-Cholesterol, HDL-Cholesterol, Apo B, and triglycerides. All methods used were AOAC approved methods.

G. Statistical Analyses of the Data

All the parameters were statistically analyzed, using changes from baseline values (0-time) to the end of study according to analyses of variance (Yanagava et al., *Biometrics*, 40:301–311, 1984.) These data were compared among the three products.

Results

Table II summarizes the study of both Type I subjects on glycemic and lipidemic parameters, while Table III provides the data for the Type II subjects.

H. Type I Study

A total of 45 subjects with clinically established Type I diabetes mellitus were randomly treated with RiceX rice bran products either in sequence or singularly as mentioned above. A total of 22 subjects were treated with product A, 26 subjects with product B and 20 subjects with product C. The pooled averages of the data on glycemic and lipid parameters of the three products are given in Table II.

I. Type II Study

A total of 41 subjects with clinically established Type II diabetes mellitus were randomly treated with $Rice_x$ Rice Bran products either singularly or in sequence as given in the protocol. A total of 23 subjects were treated with product A, 31 subjects with product B and 26 subjects with product C. The pooled averages of the data on glycemic and lipid parameters of all the three products are given in Table III.

J. Glycemic control

The results showed that there was a statistically significant (p=0.05) reduction in the glycosylated hemoglobin, by 11% when RiceX Ricelin was provided and by 10% when RiceX Fiber Complex was provided to the Type I subjects for eight weeks. A similar statistically significant (p=0.05) reduction in glycosylated hemoglobin in Type II subjects was shown. RiceX Ricelin consumption for eight weeks led to a 10% reduction in glycosylated hemoglobin, while RiceX Fiber Complex consumption for eight weeks lead to an 11% reduction. Fasting serum glucose indicated a statistically significant (p<0.5) reduction of 33%, when compared to the initial values, after eight weeks consumption of RiceX Ricelin in both Type I and Type II subjects. The RiceX Fiber Complex also showed a decrease in the fasting glucose levels of venous blood analysis of 19% and 22% in Type I and Type II respectively, when compared to initial time values.

Type I subjects who consumed or RiceX Ricelin for eight weeks showed a decrease of 16% and 14% respectively for fasting glucose and glucose measured a ½ hour before dinner (monitored by glucometer). While RiceX Fiber Complex consumption showed a decrease of 10% and 17% respectively for serum fasting glucose and serum glucose measured a ½ hour before dinner (monitored by glucometer).

In Type II subjects a decrease of 8% and 5% in fasting glucose and glucose ½ hr before dinner (monitored by glucometer) with RiceX Ricelin consumption for eight weeks was observed. A 10% reduction in both the parameters with RiceX Fiber Complex was observed.

These data on glycemic parameters indicate that RiceX products significantly control and manage blood glucose levels in diabetes mellitus. More specifically, the reduction of glycosylated hemoglobin indicated that, in these subjects, consumption of RiceX Ricelin and RiceX Fiber Complex aided in increased control of blood glucose.

K. Lipid Parameters

Total cholesterol, LDL-Cholesterol, Apo B, and triglycerides of Type I subjects who consumed RiceX Fiber Complex for eight weeks were reduced 10%, 16%, 10%, and 7% respectively, when compared to zero-time values. There was no change in HDL-Cholesterol.

A greater reduction in lipid parameters was seen in Type II subjects than that noted in Type I subjects. Total cholesterol, LDL-Cholesterol, Apo B, and triglycerides were reduced by 12%, 15%, 10% and 8% respectively when compared to zero-time values. There was no change in HDL-Cholesterol concentrations after the consumption of RiceX Fiber Complex. These results indicate that the RiceX Fiber Complex significantly controls hyperlipidemia.

TABLE II

Results of Type I (IDDM) Subjects

| | Product A (n = 22) | | | Product B (n = 26) | | | Product C (n = 20) | | |
|---|---|---|---|---|---|---|---|---|---|
| | Before | After | % Change | Before | After | % Change | Before | After | % Change |
| Glycemic parameters Phlebotomy Data | | | | | | | | | |
| Glycosylated Hb (%) | 10.91 | 10.92 | 0 | 11.25 | 10.06 | −11 | 11.32 | 10.23 | −10 |
| Fasting Serum Glucose (mg/dl) | 172.00 | 157.99 | −9 | 174.16 | 116.97 | −33 | 162.78 | 131.56 | −19 |
| Serum insulin (microunits/ml) | 49.36 | 49.71 | 0 | 52.75 | 54.86 | 4 | 52.03 | 51.99 | 0 |
| Glucometer Data | | | | | | | | | |
| Fasting Glucose (mg/dl) | 159.45 | 154.95 | −3 | 162.5 | 137.23 | −16 | 164.95 | 147.85 | −10 |
| Glucose 1/2 hr. before dinner (mg/dl) | 175.00 | 165.91 | −5 | 168.12 | 145.35 | −14 | 175.35 | 144.95 | −17 |
| Lipid Parameters | | | | | | | | | |
| Serum Total Cholesterol (mg/dl) | 181.91 | 180.07 | −1 | 174.27 | 166.14 | −5 | 185.52 | 167.74 | −10 |
| Serum LDL-Cholesterol (mg/dl) | 137.71 | 134.16 | −3 | 130.79 | 122.35 | −6 | 134.41 | 113.55 | −16 |
| Serum Apo B(mg/dl) | 88.15 | 86.15 | −2 | 85.69 | 82.708 | −5 | 84.37 | 75.96 | −10 |

TABLE II-continued

Results of Type I (IDDM) Subjects

| | Product A (n = 22) | | | Product B (n = 26) | | | Product C (n = 20) | | |
|---|---|---|---|---|---|---|---|---|---|
| | Before | After | % Change | Before | After | % Change | Before | After | % Change |
| Serum Triglycerides (mg/dl) | 135.36 | 134.85 | 0 | 134.07 | 130.13 | −3 | 129.76 | 120.58 | −7 |
| Serum HDL-Cholesterol (mg/dl) | 37.65 | 37.62 | 0 | 38.73 | 38.07 | −2 | 39.29 | 39.57 | 0 |

TABLE III

Results of Type II (NIDDM) Subjects

| | Product A (n = 23) | | | Product B (n = 31) | | | Product C (n = 26) | | |
|---|---|---|---|---|---|---|---|---|---|
| | Before | After | % Change | Before | After | % Change | Before | After | % Change |
| Glycemic parameters Phlebotomy Data | | | | | | | | | |
| Glycosylated Hb (%) | 10.22 | 10.63 | 4 | 10.69 | 9.65 | −10 | 10.700 | 9.51 | −11 |
| Fasting Serum Glucose (mg/dl) | 158.11 | 142.28 | −10 | 158.18 | 106.52 | −33 | 145.42 | 113.65 | −22 |
| Serum insulin (tricrounits/ml) | 49.42 | 49.98 | 0 | 48.48 | 50.31 | 4 | 49.45 | 49.94 | 0 |
| Glucometer Data | | | | | | | | | |
| Fasting Glucose (mg/dl) | 120.13 | 121.71 | 1 | 128.45 | 118.16 | −8 | 129.12 | 115.73 | −10 |
| Glucose 1/2 hr. before dinner (mg/dl) | 120.17 | 129.91 | 8 | 129.68 | 123.61 | −5 | 134.54 | 120.96 | −10 |
| Lipid Parameters | | | | | | | | | |
| Serum Total Cholesterol (mg/dl) | 182.81 | 172.79 | −5 | 181.14 | 171.1 | −6 | 186.04 | 164.58 | −12 |
| Serum LDL-Cholesterol (mg/dl) | 146.02 | 134.97 | −8 | 143.18 | 131.48 | −8 | 146.46 | 124.77 | −15 |
| Serum Apo B (mg/dl) | 95.56 | 94.23 | −1 | 94.92 | 92.27 | −3 | 95.00 | 85.62 | −10 |
| Serum Triglycerides (mg/dl) | 143.75 | 139.13 | −3 | 138.85 | 135.47 | −2 | 143.01 | 131.24 | −8 |
| Serum HDL-Cholesterol (mg/dl) | 36.23 | 36.21 | 0 | 34.42 | 34.33 | 0 | 33.64 | 33.54 | 0 |

Example 2

This example illustrates the synthesis of enzyme treated stabilized rice bran.

Twelve hundred pounds of stabilized rice bran was mixed with five hundred seventy gallons of water to form a water extract. The mixture was allowed to agitate for thirty minutes. Two hundred and forty grams of α-amylase (Solvay Enzymes, Elkhart, Ind.) were added and allowed to mix for ten minutes. Thereafter the mixture was pumped through a heat exchanger set at about 190° F. and allowed to travel through a pipe coil for 25 minutes. The mixture was then dried on a drum dryer to a moisture level below 5%.

Example 3

This example illustrates the synthesis of stabilized rice bran insoluble and soluble derivatives.

Twelve hundred pounds of stabilized rice bran was mixed with five hundred seventy gallons of water to form a water extract. The mixture was allowed to agitate for thirty minutes. Two hundred and forty grams of α-amylase were added to the mixture and allowed to mix for ten minutes. Thereafter the mixture was pumped through a heat exchanger set at about 190° F. and allowed to travel through a pipe coil for 25 minutes. The mixture was then pumped to a horizontal decanting centrifuge set at 3,600 RPM and fed at a rate of two gallons per minute. The soluble fraction of the rice bran was separated from the insoluble fraction in the centrifuge. The soluble fraction was then dried on a drum dryer to 2.8 % moisture. The insoluble fraction was also dried on a drum dryer to 4% moisture. This process yielded 550 lbs. of dried rice bran insolubles and 420 lbs. of dried rice bran soluble concentrate. The chemical composition of the two products are set forth in Tables IV and V respectfully.

Example 4

This example sets forth Tables IV–VII which tabulates components of stabilized rice bran derivatives.

TABLE IV

RiceX ™ FIBER COMPLEX

| MACRONUTRIENTS | |
|---|---|
| Protein | 20.5% |
| Fat | 13.4% |
| Total Dietary Fiber | 49.5% |
| (Soluble Fiber 0–1%) | |
| Carbohydrates | 3.0% |
| Ash | 10.0% |
| Moisture | 3.5% |

| MICRONUTRIENTS | |
|---|---|
| Water Soluble Vitamins (mg/100 Grams) | Average |
| Thiamine | 2.00 |
| Riboflavin | 0.19 |
| Niacin | 30.55 |
| Pantothenic Acid | 1.90 |
| Vitamin $B_6$ | 1.67 |
| Biotin | 0.011 |
| Minerals (mg/100 Grams) | Average |
| Sodium | 16.0 |
| Calcium | 92.5 |
| Magnesium | 1223.3 |
| Potassium | 1670.0 |
| Vitamin E and Other "Tocol's" (mg/100 Grams) | Average |
| α-Tocopherol | 0.74 |
| γ-Tocopoherol | 0.40 |
| δ-Tocopherol | 0.43 |
| Total Tocopherols (T) | 1.19 |
| Tocotrienols | |
| Tocotrienols | 0.59 |
| Tocotrienol | 1.55 |
| Tocotrienol | 1.60 |
| Tocotrienol | 0.19 |
| Total Tocotrienols ($T_3$) | 2.54 |
| Total TOCOLS (T + $T_3$) | 3.73 |
| Vitamin A and Other Carotenoids (µg/100 Grams) | Average |
| α-Carotene | TBD |
| β-Carotene | TBD |
| Lycopene | TBD |
| Pre-Lutein | TBD |
| Lutein | TBD |
| Zeaxantin | TBD |
| Pre-Cryptoxanthin | TBD |
| Cryptoxanthin | TBD |
| β-Cryptoxanthin | TBD |
| Total CAROTENOIDS | TBD |
| τ-Oryzanol (mg/100 Grams) | Average |
| | 174.1 |
| Phytosterols (mg/100 Grams) | Average |
| Sitosterol | 146.46 |
| Brassicasterol | 13.20 |
| Campesterol | 90.40 |
| Stigmesterol | 67.15 |
| Total PHYTOSTEROLS | 317.2 |

TABLE V

RiceX RICELIN ™

| MACRONUTRIENTS | |
|---|---|
| Protein | 7.5% |
| Fat | 26.5% |
| Total Dietary Fiber | 3.0% |
| Carbohydrates | 54.5% |
| Ash | 5.0% |
| Moisture | 3.0% |

| MICRONUTRIENTS | |
|---|---|
| Water Soluble Vitamins (mg/100 Grams) | Average |
| Thiamine | 3.64 |
| Riboflavin | 0.46 |
| Niacin | 76.6 |
| Pantothenic Acid | 5.82 |
| Vitamin $B_6$ | 5.81 |
| Biotin | 0.015 |
| Minerals (mg/100 Grams) | Average |
| Sodium | 15.75 |
| Calcium | 8.33 |
| Magnesium | 170.8 |
| Potassium | 1562.0 |
| Vitamin E and Other "Tocol's" (mg/100 Grams) | Average |
| α-Tocopherol | 6.80 |
| γ-Tocopoherol | 1.13 |
| δ-Tocopherol | 0.07 |
| Total Tocopherols (T) | 3.00 |
| αTocotrienol | 4.90 |
| β-Tocotrienol | 0.36 |
| γ-Tocotrienol | 4.48 |
| δ-Tocotrienol | 0.30 |
| Total Tocotrienols ($T_3$) | 10.0 |
| Total TOCOLS (T + $T_3$) | 18.0 |
| Vitamin A and Other Carotenoids (µg/100 g) | Average |
| α-Carotene | TBD |
| β-Carotene | TBD |
| Lycopene | TBD |
| Pre-Lutein | TBD |
| Lutein | TBD |
| Zeaxantin | TBD |
| Pre-Cryptoxanthin | TBD |
| Cryptoxanthin | TBD |
| β-Cryptoxanthin | TBD |
| Total CAROTENOIDS | TBD |
| τ-Oryzanol (mg/100 Grams) | Average |
| | 248.1 |
| Phytosterols (mg/100 Grams) | Average |
| Sitosterol | 211.90 |
| Brassicasterol | 15.20 |
| Campesterol | 117.32 |
| Stigmesterol | 68.69 |
| Total PHYTOSTEROLS | 385.0 |

TABLE VI

RiceX ™ STABILIZED RICE BRAN

MACRONUTRIENTS

| | |
|---|---|
| Protein | 14.5% |
| Fat | 20.5% |
| Total Dietary Fiber | 29.0% |
| (Soluble Fiber 2–6%) | |
| Carbohydrates | 22.0% |
| Ash | 8.0% |
| Moisture | 6.0% |

MICRONUTRIENTS

| Water Soluble Vitamins (mg/100 Grams) | Average |
|---|---|
| Thiamine | 2.65 |
| Riboflavin | 0.28 |
| Niacin | 46.87 |
| Pantothenic Acid | 3.98 |
| Vitamin $B_6$ | 3.17 |
| Biotin | 0.014 |

| Minerals (mg/100 Grams) | Average |
|---|---|
| Sodium | 8.0 |
| Calcium | 39.7 |
| Magnesium | 727.0 |
| Potassium | 1573.0 |

| Vitamin E and Other "Tocol's" (mg/100 Grams) | Average |
|---|---|
| α-Tocopherol | 10.60 |
| γ-Tocopoherol | 1.34 |
| δ-Tocopherol | 0.07 |
| Total Tocopherols (T) | 11.97 |
| α-Tocotrienol | 7.56 |
| β-Tocotrienol | 0.41 |
| γ-Tocotrienol | 5.36 |
| δ-Tocotrienol | 0.31 |
| Total Tocotrienols ($T_3$) | 13.60 |
| Total TOCOLS (T + $T_3$) | 25.61 |

| Vitamin A and Other Carotenoids (μg/100 Grams) | Average |
|---|---|
| α-Carotene | 0.4 |
| β-Carotene | 37.0 |
| Lycopene | 2.3 |
| Pre-Lutein | ND |
| Lutein | 63.8 |
| Zeaxantin | 18.4 |
| Pre-Cryptoxanthin | 7.4 |
| Cryptoxanthin | ND |
| β-Cryptoxanthin | ND |
| Total CAROTENOIDS | 129.3 |

| τ-Oryzanol (mg/100 Grams) | Average |
|---|---|
| | 245.15 |

| Phytosterols (mg/100 Grams) | Average |
|---|---|
| Sitosterol | 151.47 |
| Brassicasterol | 14.61 |
| Campesterol | 91.57 |
| Stigmesterol | 58.59 |
| Total PHYTOSTEROLS | 302 |

TABLE VII

Antioxidants in RiceX ™ STABILIZED RICE BRAN

A. τ-Oryzanol: (ppm) (2206–3000)
  Cycloartenyl Ferulate
  24-Methylene Cycloartanyl Ferulate
  Campesteryl Ferulate
  β-Sitosteryl Ferulate
  Stigmasteryl Ferulate
B. Tocopherols & Tocotrienols: (220–320 ppm)
  α-Tocopherol
  β-Tocopherol
  τ-Tocopherol
  δ-Tocopherol
  α-Tocotrienol
  β-Tocotrienol
  τ-Tocotrienol
  Tocotrienols (Artifacts)
C. Phytosterols: (2230–4400 ppm)
  4-Demethylsterols, 4-Methyl Sterol & Brassino Steriods
  β-Sitosterol
  Campesterol
  Stigmasterol
  Δ5 Avinsterol
  Δ7 Stigmastenol
  Isofucosterol
  β-Amyrin
  Gramisterol
  Citrostadienol
  Obtusifoliol
  Branosterol
  28-Homotyphasterol
  28-Homosteasternoic Acid
  6-Deoxycastasterone
J. Enzymes:
  Gluthathione Peroxidase
  Methionine Reductase
  Super Oxide Dismutase
  Polyphenol Oxidase
  Aspartate Amino Transferase Isoenzyme
  AAT-1
  AAT-2
  Coenzyme Q1O
K. Polysaccharides:
  Cycloartenol Ferulic Acid Glycoside
  Diferulic Acid Complex
  Diferulic Acid + 3
  Glucose + 2
  Calcium ions complex
D. Amino Acids: (ppm)
  Tryptophan (2100)
  Histidine (3800)
  Methionine (2500)
  Cystine (336–448)
  Cysteine (3200)
  Arginine (10800)
E. Polyphenols:
  α-Lipoic Acid
  Ferulic Acid
  Methyl Ferulate
  p-Coumaric Acid
  p-Sinapic Acid
F. Flavones and Proantho-cyanidins
  Iso Vitexin
  Flavone Glycosides
  Olegomeric Proanthocyanidins
G. Other Antioxidants: (ppm)
  Inositol/Myo Inositol (1200–1880)
  Phytic Acid/Phytates (1500–1710
  Biotin (0.1–0.22)
  Choline (930–1150)
H. Carotenoids: (0.9–1.6 ppm)
  α-carotene
  β-carotene
  Lycopene
  Lutein
  Zeasanthine
I. Phospholipids:
  Phosphatidyl Choline
  Phosphatidyl Ethanolamine
  Lysolecithin
L. Metal Chelators: (ppm)
  Magnesium (6250–8440)
  Calcium (303–500)
  Phosphorous (14700–17000)
M. B-Complex Vitamins: (ppm)
  Thiamine (22–31)
  Riboflavin (2.2–3.5)
  Niacin (370–660)
  Pantothenic Acid (36–50)
  Pyridoxine (29–42)

All publications, patents and patent applications mentioned in this specification are herein incorporated by reference into the specification in their entirety for all purposes.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A method for reducing mammalian serum total cholesterol, LDL cholesterol, apolipoprotein B and triglyceride levels in a mammal, said method comprising:
  ingesting a stabilized rice bran derivative selected from the group consisting of an enzyme treated stabilized rice bran, an insolubilized fraction and mixtures thereof, thereby reducing serum total cholesterol, LDL cholesterol, apoliprotein B and triglyceride levels in said mammal.

2. The method according to claim 1, wherein said mammal is a human.

3. The method according to claim 2, wherein said mammal is suffering from hyperlipidemia.

4. The method according to claim 2, wherein said mammal is suffering from cardiovascular disease.

5. The method according to claim 2, wherein said mammal is suffering from atherosclerosis.

6. The method according to claim 2, wherein said mammal is suffering from arteriosclerosis.

7. The method according to claim 2, wherein said mammal is suffering from xanthomatosis.

8. The method according to claim 1, wherein said rice bran derivative is an enzyme treated stabilized rice bran derivative.

9. The method according to claim 8, wherein said enzyme treated rice bran derivative comprises about 40% to about 60% total dietary fiber content w/w.

10. The method according to claim 1, wherein said rice bran derivative is an insolubilized fraction.

11. The method according to claim 10, wherein said rice bran derivative is an insolubilized fraction comprising about 40% to about 60% total dietary fiber content w/w.

12. The method according to claim 10, wherein said rice bran derivative is an insolubilized fraction comprising about 1% to about 20% total non-fiber carbohydrate content w/w.

13. The method according to claim 10, wherein said rice bran derivative is an insolubilized fraction comprising about 10% to about 20% total fat content w/w.

14. The method according to claim 10, wherein said rice bran derivative is an insolubilized fraction comprising about 15% to about 25% total protein content w/w.

15. The method according to claim 2, wherein said derivative is ingested in an amount of about 10 grams to about 100 grams per day total.

16. The method according to claim 15, wherein said amount is ingested in at least 2 doses.

17. The method according to claim 15, wherein said amount is about 10 grams to about 40 grams per day total.

18. The method according to claim 15, wherein said amount is about 15 grams to about 30 grams per day total.

19. A method for reducing triglyceride levels in mammalian serum in a mammal, said method comprising:

ingesting a stabilized rice bran derivative selected from the group consisting of an enzyme treated stabilized rice bran derivative, an insolubilized fraction and mixtures thereof, thereby reducing said triglyceride levels in said mammalian serum.

20. The method according to claim 19, wherein said mammal is a human.

21. The method according to claim 19, wherein said rice bran derivative is an enzyme treated stabilized rice bran derivative.

22. The method according to claim 19, wherein said rice bran derivative is an insolubilized fraction.

23. A method for reducing apolipoprotein B levels in mammalian serum in a mammal, said method comprising:

ingesting a stabilized rice bran derivative selected from the group consisting of an enzyme treated stabilized rice bran derivative, an insolubilized fraction and mixtures thereof, thereby reducing said apolipoprotein B levels in said mammalian serum.

24. The method according to claim 23, wherein said mammal is a human.

25. The method according to claim 23, wherein said rice bran derivative is an enzyme treated stabilized rice bran derivative.

26. The method according to claim 23, wherein said rice bran derivative is an insolubilized fraction.

* * * * *

UNITED STATES PATENT AND TRADEMARK OFFICE
CERTIFICATE OF CORRECTION

| | |
|---|---|
| PATENT NO. | : 6,126,943 |
| DATED | : October 2, 2000 |
| INVENTOR(S) | : Cheruvanky et al. |

Page 1 of 1

It is certified that error appears in the above-identified patent and that said Letters Patent is hereby corrected as shown below:

<u>Title page,</u>
Item [75], Inventors: Rukmini Cheruvanky, Folsom,
                  Patricia McPeak; Reddy Sastry V. Cherukuri, both of El Dorado Hills, all of CA;
                  Ike E. Lynch, Dillon, Mont.;
                  Asaf A. Qureshi, Madison, WI.

Signed and Sealed this

First Day of January, 2002

*Attest:*

*Attesting Officer*

JAMES E. ROGAN
*Director of the United States Patent and Trademark Office*